(12) United States Patent
Pitarelli

(10) Patent No.: US 7,850,508 B2
(45) Date of Patent: Dec. 14, 2010

(54) POST-SURGICAL MEDICAL DEVICE FOR QUADRECTOMY, MASTECTOMY AND/OR MAMMARY SURGERY

(75) Inventor: Carla Pitarelli, Rome (IT)

(73) Assignee: Di Segni Umberto, Rome (IT)

( * ) Notice: Subject to any disclaimer, the term of this patent is extended or adjusted under 35 U.S.C. 154(b) by 639 days.

(21) Appl. No.: 11/836,305

(22) Filed: Aug. 9, 2007

(65) Prior Publication Data

US 2007/0275635 A1    Nov. 29, 2007

(51) Int. Cl.
*A41C 3/00*    (2006.01)
(52) U.S. Cl. .......................................... 450/85; 450/86
(58) Field of Classification Search ............... 450/3–11, 450/15–17, 20, 21, 25, 26, 28, 30, 31, 34, 450/65, 66, 70, 58, 75–79; 602/19, 41, 53, 602/61, 75, 76; 2/67, 69, 73, 102, 104, 105, 2/106, 109, 110, 113, 114, 463; 128/874, 128/99.1, 101.1, 845, 846
See application file for complete search history.

(56) References Cited

U.S. PATENT DOCUMENTS

| | | | |
|---|---|---|---|
| 9,496 A * | 12/1852 | McGee | 33/756 |
| 272,179 A * | 2/1883 | Williams | 450/18 |
| 513,086 A * | 1/1894 | Chambers | 450/58 |
| 657,133 A * | 9/1900 | Redick | 450/15 |
| 897,480 A * | 9/1908 | Olmsted | 450/142 |
| 1,082,085 A * | 12/1913 | Keitel | 450/54 |
| 1,126,207 A * | 1/1915 | Hayes | 450/15 |
| 1,267,657 A * | 5/1918 | Grace | 450/18 |
| 1,868,391 A * | 7/1932 | Kispert | 450/9 |
| 2,121,088 A * | 6/1938 | La Rue | 450/36 |
| 2,180,390 A * | 11/1939 | Blair | 450/18 |
| 2,392,724 A * | 1/1946 | Cohen | 450/8 |
| 2,717,602 A * | 9/1955 | Radler | 623/7 |
| 5,098,331 A | 3/1992 | Corrado et al. | |
| 6,135,975 A | 10/2000 | Johnstone et al. | |
| 7,144,294 B2 * | 12/2006 | Bell et al. | 450/20 |

FOREIGN PATENT DOCUMENTS

FR    1366993 A    7/1964

* cited by examiner

*Primary Examiner*—Gloria Hale
(74) *Attorney, Agent, or Firm*—Gauthier & Connors LLP

(57) ABSTRACT

Post-surgical medical device for quadrectomy, mastectomy and/or mammary surgery, comprising a support and containing corset divided into at least two parts, respectively front part and rear part, tightened about patient thorax, said corset supporting a cups bra, and providing at least two bandage bands that are passed about the patient thorax, crossing them many times, to be finally fixed giving the proper containment function without using adhesive tapes.

11 Claims, 3 Drawing Sheets

POST-SURGICAL MEDICAL DEVICE FOR QUADRECTOMY, MASTECTOMY AND/OR MAMMARY SURGERY

PRIORITY INFORMATION

This application claims benefit of International Patent Application No. PCT/EP2006/050632, filed on Feb. 2, 2006 and claims priority to German Patent Application No. 20 2005 001 716.7, filed on Feb. 3, 2005 all of which are incorporated herein in their entirety.

BACKGROUND OF THE INVENTION

1. Field of the Invention

The present invention relates to the post-surgical field, with particular reference to the quadrectomy, mastectomy and generally speaking to mammary surgery, including aesthetical and/or reconstructive surgery.

2. Brief Description of the Art

Containing bras are usually suggested after quadrectomy or mastectomy intervention, for breasts subjected to surgical trauma, since more or less large tissue parts are ablated, and the organ is modified and reconstructed. There is a drastic intervention on the basis of the specific pathology for each case and on the basis of the age of each patient, since some times the whole organ is ablated, while other times the glands lymphatic axillary and all or part of underlying muscular tissues are also ablated. This modification of the woman body involves a psychical and physical sufferance. In any case, the femininity is modified at the physical level.

After the intervention, the patient wakes up with the thorax fully dressed by adhesive tapes that the surgery employees for medication; from the waist to the neck it seems as if a body-armour holds tight and models the new breast shape.

The problem for the women is that, in the days following the surgical interventions, the bandage band must be daily removed for medication and controls, and it is made up again immediately after the medication.

After 4/5 days, dressings are finally removed. The thorax is flared, the skin is inflamed since it did not breath and many zones are present on which adhesive tape remains. The glue having to be removed by oil.

Due to this procedure, elder women can be subjected to bedsores. This risk is higher during the hot season, but the skin inflammation drawback is present independently from the age. The thorax and breast are fully swollen and turgid. This problem occurs for about 30/40 days after the surgical intervention.

Swelling is diffused and furthermore, if lymph glands are removed, also zones under, in front of and behind the axillary zone swell, sometimes interestingly also the arm can often cause liquid effusion, thus requiring drawing by syringe. This is a post-surgery procedure.

At present, many calibrated bras and containing corsets are available on the market.

However, calibrated bras (i.e with a large cup and small corset or vice versa) provided with more or less elastic cups, are difficult to find and cannot suitably fit with the real build of the patient.

Containing corsets can have interchangeable cups or they can have zip-fasteners, but they have a shape not always corresponding to the shape of the patient.

To this end, it is an important underlying that present bras and corsets in any case require the use of bandages, at least during the very first days after the surgical intervention.

Beside, the products in any case are not fully satisfying: bras do not provide the tightening of the various swelling axillary and dorsal parts and, furthermore, if for some reasons they must be elastic, on the other hand, when woman moves, the breast too moves while it should remain still.

Corsets are not calibrated, i.e. it is not possible to conform their cup-thorax ratio. They have a zip-fastener closure or a hook closure (thus not being possible to enlarge the corset beyond a set dimension). Even if interchangeable cups are present, they cannot be enlarged or narrowed at will. Thus, swelling containment is not sufficiently carried out.

A first disadvantage of the products known on the market is that they cannot be used to replace bandages.

A second disadvantage is that the adjustment of corsets and/or bras for conforming the same to the patient is almost null, or very reduced, thus not permitting a suitable containment and a suitable modelling of tissues subjected to the surgical intervention.

SUMMARY OF THE INVENTION

The main object of the present invention is that of solving the above problems, including providing a bra-corset-bandage suitable to be directly applied to the patient immediately after the surgical intervention, thus eliminating the noisy adhesive tape-bandage and comfortably accompanying the patient all along the post-surgical period.

This object has been reached, according to the invention, realising a support and containing corset substantially divided into four parts: two lateral—front parts and two lateral—rear parts. The corset supporting two fixed or removable cups, and providing two bandage bands that are passed about the patient thorax, crossing them many times, and that are then fixed giving the proper containment function without using adhesive tapes.

BRIEF DESCRIPTION OF THE DRAWINGS

A better understanding of the invention will be obtained by the following detailed description and with reference to the figures of the enclosed drawings, showing now described, for illustrative but not limitative purposes a preferred embodiment.

DETAILED DESCRIPTION OF THE INVENTION

Making now reference to the above-mentioned figures, the medical device according to the present invention substantially comprises the following elements:

bra: comprising two cups 1 having shape and dimension suitable to the patient needing the device, the cups being preferably, but not exclusively, removable;

bodice: supporting the cups 1, it is comprised of four parts or "quadrants", two lateral—front parts 2A and two lateral—rear parts 2P, wrapping the patient thorax;

bandage band: comprised of long bands 3, preferably fixed to the upper side of the rear quadrants 2P, passing on the shoulder and crossed both on the front and on the rear of the patient thorax, in order to maintain the bodice well adhering the body, thus conforming to the reduction of the post-surgical swelling.

Bra cups 1 are chosen on the basis of the patient breast size, thus giving the maximum containment of the zones subjected to the surgical intervention.

Bodice is tightened on the patient body and quadrants 2A-2P comprising the same are restrained each other conforming to the patient shape, in function of her body.

In the illustrative example described, quadrants 2A-2P comprising bodice are tied by the laces 4, tightening of which can be different on the front and on the rear sides and/or on the right and on the left sides. The laces 4 are provided near the four openings (front, rear, right and left) between the four bodice quadrants 2A-2P, and have such a length to permit an adjustment of the dimension of each opening, the dimension preferably ranging between about 0 and 10 cm.

Cups 1 and bodice tissue is of the transpiring (breathable) and elastic—containing kind, and stiffening and support sticks are provided in the bodice, the sticks being preferably provided in a substantially vertical position.

According to a peculiar feature of the invention, bodice and bra described perfectly follow the patient body modification (with particular reference to the progressive reduction of swelling) all along the post-surgical course and the convalescence.

Beside, bandage band 3 crossing in the front and on the rear, is passed above and under the breast, thus tightening at the same time the part under axillas and about the breasts and behind the shoulders, thus ensuring an efficient containment and support action of tissues traumatized by the surgical intervention.

This feature is very important, since besides completely avoiding the need of adhesive tapes, permits to the patient of having a bodice exactly conforming to her size and to the dimension and postural variation of her body.

Figure 1:
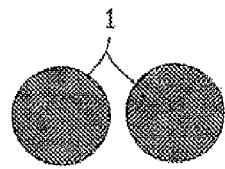
FIG. 1 schematically shows bra cups according to the invention.
Figure 3:
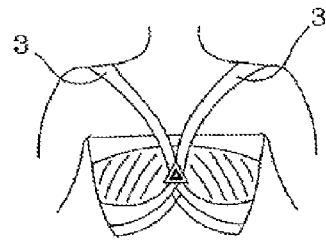
FIG. 3 shows a front view of the inventive solution, put on the patient.
Figure 2:
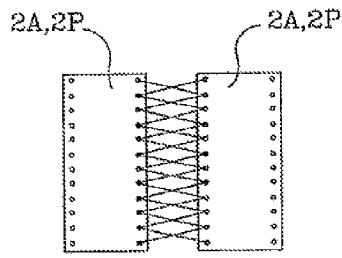
FIG. 2 schematically shows the laces for tightening the parts comprising the corset about the patient body.
Figure 4:
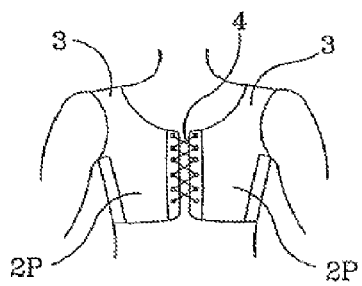
FIG. 4 shows the rear part of the inventive solution.
Figure 5:
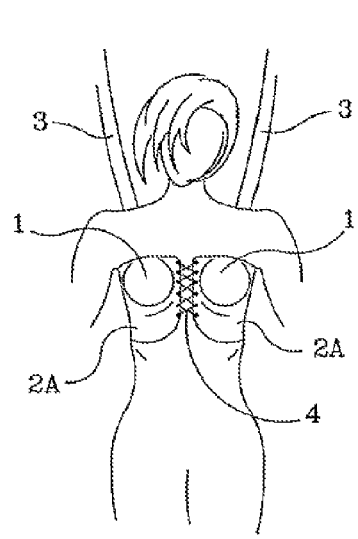
FIGS. 5, 6 and 7 show different views of the inventive solution before wrapping with shoulders.
Figure 6:
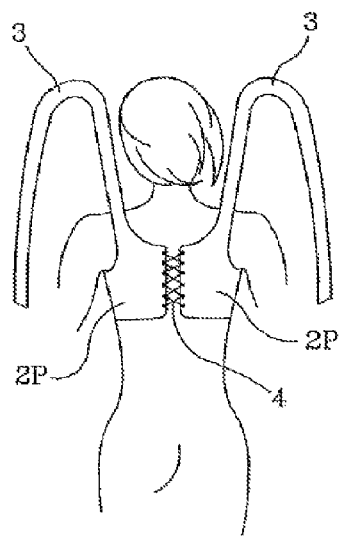
Figure 7:
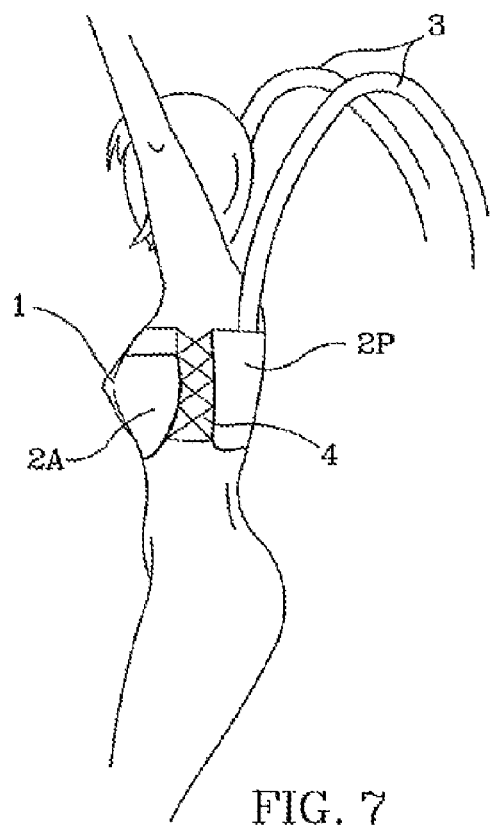
Figure 8:
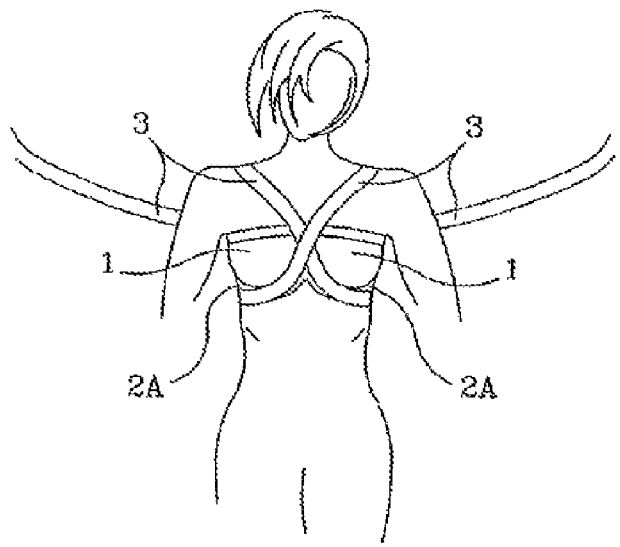
FIGS. 8-11 show the different steps of bandage band with bands—shoulders.
Figure 9:
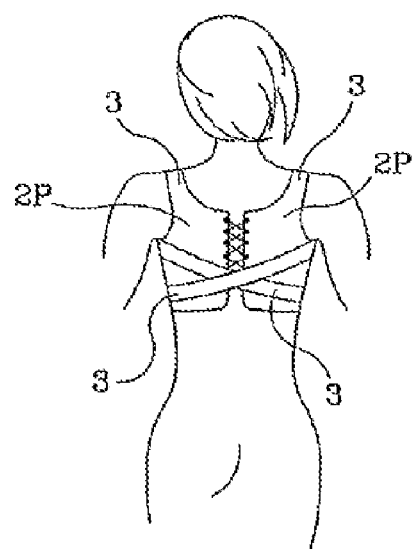
Figure 10:
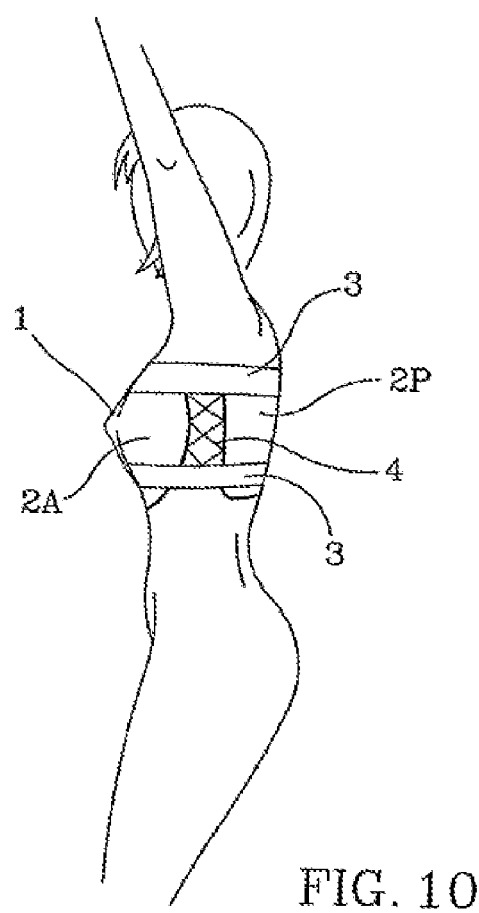
Figure 11:
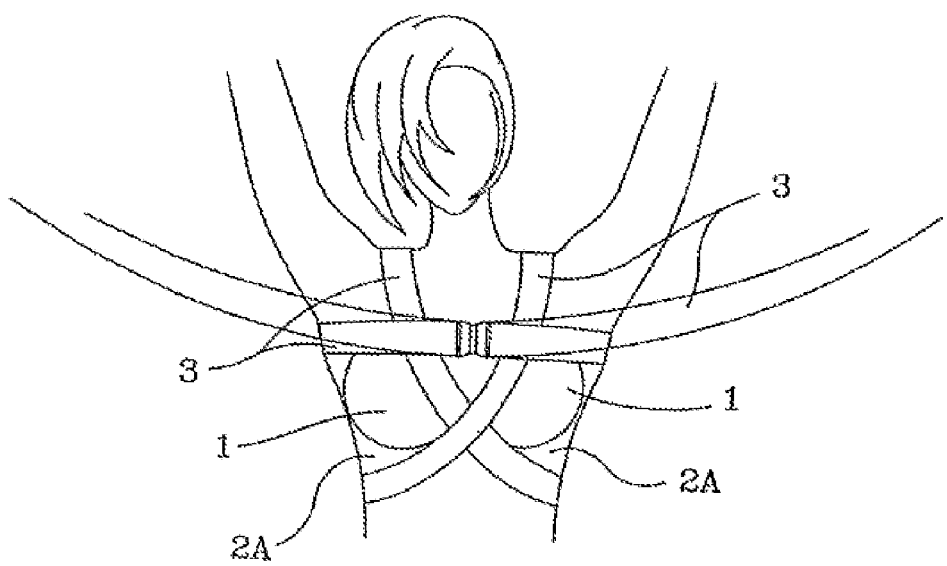

As clearly shown in the figures, once chosen cups 1 having dimensions suitable for the breast, they are coupled to the front quadrants 2A of the bodice, that is put on by the patient, tightening the front, rear and lateral laces 4 according to her needing and sensation (FIGS. 1-3).

Now, the patient makes the bandage band 3 passing above shoulders, crossing them in the front between the breasts and turning downward about the same, and then makes them passing laterally toward the back, crossing once again on the back, going back on the front side, passing under axillas and lacing or fixing them above the breast (FIGS. 3-7).

In this way, the shoulders 3 advantageously make a bandage band with a beneficial function of compression of all the post-surgical swelling.

The final fixing of the bandage band or shoulders 3 each other can be carried out in different ways, such as for example by a suitable buckle, or by VELCRO® (hook and loop fasteners), or hooks and rings, or by a simple knot, or in any other suitable way.

Finally, it is important noting that the medical device described in the above, thanks to its adaptability and adjustability features, can be used immediately after the surgical intervention, following the anatomical profile of the patient and advantageously permitting properly positioning drainage tubes (front, rear, and/or lateral) eventually necessary for wound draining in order to facilitate cicatrisation and post-surgical course.

To this end, it is worthwhile noting that according to the present invention, it is also possible using, in function of the anatomical needing of the patient, front quadrants 2A with different sizes with respect to rear quadrants 2P, just to better conform to patient physique.

Finally, a simplified arrangement of the invention can provide that the front 2A and rear 2P quadrants are, at least one front quadrant and one rear quadrant, tied to the patient body only by lateral laces.

It is also preferable that the lower part of front quadrants 2A is shaped in so shaped not to cover the part under the breastbone (corresponding to the so called ("stomach mouth"), thus permitting all the thorax movements without causing troubles to the patient while seating or bending forward.

The present invention has been described for illustrative but not limitative purposes, according to its preferred embodiments, but it is to be understood that modifications and/or changes can be introduced by those skilled in the art without departing from the relevant scope as defined in the enclosed claims.

I claim:

1. A post-surgical medical device for quadrectomy, mastectomy and/or mammary surgery, said device comprises a support containing a corset divided into at least two parts, respectively a front part and a rear part, tightened about a patient's thorax, said corset supporting bra cups, and having at least two bands that are passed about the patient's thorax, wherein said bands are long enough to cross the patient's thorax multiple times, fixed wherein the bands are secured in place giving the proper containment and support of the breasts after surgery without using adhesive tapes to directly cover any wounds.

2. The medical device according to claim 1, wherein the device comprises:
    a bra: comprising two cups according to anatomical conformation of the patient;
    a bodice: supporting said cups, said bodice comprised of four parts or quadrants, including two lateral front parts and two lateral-rear parts, which wrap around the patient's thorax;
    bands: comprised of long bands or shoulder straps, fixed to an upper side of the rear quadrants of said bodice, passing on shoulder's of the patient and crossed both on the front and on the rear of the patient's thorax, in order to maintain said bodice tightly against the body, thus conforming to reduce the natural swelling of the post-surgical procedure.

3. The medical device according to claim 2, wherein said bodice is suitable to be tightened about the patient's body and quadrants comprising the same are suitable to be coupled each other, conforming to patient's body shape, in function of a patient's physique.

4. The medical device according claim 2, wherein quadrants comprising said bodice are tied to each other with laces, tightening of said laces can be different on a front and on a rear side and/or on a right and on a left side; said laces being provided near four openings including front, rear, right and left between the four bodice quadrants.

5. The medical device according to claim 4, wherein said laces have a length to permit an adjustment of the dimension of each opening between each quadrant such that said dimension of each opening between each quadrant is between about 0 and 10 cm.

6. The medical device according to claim 2, wherein the cups and bodice material is transpiring and elastic containing kind; stiffening and support sticks being provided in said bodice.

7. The medical device according to claim 1, wherein the bandage band crossing in the front and on the rear, and to pass above and under the breast according to a substantially horizontal direction, thus tightening at the same time the part under axillas and about breasts and behind shoulders, thus ensuring an efficient containment and support action of tissues traumatized by the surgical intervention; permitting to the patient of having a bodice exactly conforming to her size and to the dimension and postural variation of her body.

8. The medical device according to claim 2, wherein the band may be held in place against the bodice with a suitable buckle, or by Velcro®, or hooks and rings, or by a simple knot, or in any other suitable way; thus obtaining that shoulders make a bandage band with a beneficial function of compression of all the post-surgical swelling.

9. The medical device according to claim 1, wherein said device can be used immediately after the surgical intervention, following the anatomical profile of the patient, said device permitting properly positioning drainage tubes (front, rear, and/or lateral) eventually necessary for wound drainage in order to facilitate cicatrisation and post-surgical course.

10. The medical device according to claim 1, wherein said bra cups are removable, wherein it is possible to change them in function of the patient's breast size.

11. A post-surgical medical device for quadrectomy, mastectomy and/or mammary surgery, said device comprising:
   a support containing corset divided into four quadrants, a front left, a front right, a rear left ad a rear right quadrant, said quadrants are each laced together and then tightened around a patient's thorax;
   bra cups which cups size are dependent upon the patient's breast size and are supported by said corset; and
   at least two bands attached to upper edges of two quadrants, such that said bands are passed about the patient's thorax, said bands are long enough to cross the patient's thorax multiple times, and then secured in place giving the proper containment and support of the breasts after surgery to reduce the natural swelling of the post-surgical procedure and without using adhesive tapes to directly cover any wounds.

* * * * *